US012649911B2

(12) United States Patent
Lee et al.

(10) Patent No.: US 12,649,911 B2
(45) Date of Patent: Jun. 9, 2026

(54) RECOMBINANT ORGANISM AND METHOD

(71) Applicant: DAESANG CORPORATION, Seoul (KR)

(72) Inventors: Sun Hee Lee, Seoul (KR); Tae Yeol Choi, Seoul (KR); Hyun Ho Kim, Seoul (KR); Dong Hyun Kim, Seoul (KR); Hyun Sook Kim, Seoul (KR); Jong Hwan Shin, Seoul (KR)

(73) Assignee: DAESANG CORPORATION, Seoul (KR)

( * ) Notice: Subject to any disclaimer, the term of this patent is extended or adjusted under 35 U.S.C. 154(b) by 0 days.

(21) Appl. No.: 18/880,346

(22) PCT Filed: Aug. 31, 2023

(86) PCT No.: PCT/KR2023/012972
§ 371 (c)(1),
(2) Date: Dec. 31, 2024

(87) PCT Pub. No.: WO2024/214880
PCT Pub. Date: Oct. 17, 2024

(65) Prior Publication Data
US 2025/0257334 A1 Aug. 14, 2025

(30) Foreign Application Priority Data
Apr. 11, 2023 (KR) ........................ 10-2023-0047745

(51) Int. Cl.
*C12N 9/12* (2006.01)
*C12N 15/77* (2006.01)
*C12P 19/32* (2006.01)

(52) U.S. Cl.
CPC ........... *C12N 9/1205* (2013.01); *C12N 15/77* (2013.01); *C12P 19/32* (2013.01)

(58) Field of Classification Search
CPC ........ C12N 9/1205; C12N 15/77; C12P 19/32
See application file for complete search history.

(56) References Cited

FOREIGN PATENT DOCUMENTS

| KR | 10-1166027 | 7/2012 |
| KR | 10-2016-0078694 | 7/2016 |
| KR | 10-1904675 | 10/2018 |
| KR | 10-1916611 | 11/2018 |
| KR | 10-1916622 | 11/2018 |

OTHER PUBLICATIONS

Gilroy et al., PeerJ 9, e10941, pp. 1-142, 2021.*
Gilroy et al., GenBank HJG64367 Nov. 4, 2011.*
Gilroy et al., GenBank accession No. DYUQ01000012, Nov. 4, 2021.*
International Search Report issued Jan. 25, 2024 in International (PCT) Application No. PCT/KR2023/012972.
Krahn, Irene et al., "Evolving a New Efficient Mode of Fructose Utilization for Improved Bioproduction in. *Corynebacterium glutamicum*", Frontiers in Bioengineering and Biotechnology, May 2021, vol. 9, Article 669093, 13 pages.

* cited by examiner

*Primary Examiner* — Delia M Ramirez
(74) *Attorney, Agent, or Firm* — Wenderoth, Lind & Ponack, L.L.P.

(57) ABSTRACT

The present invention relates to a novel PTS transporter subunit EIIC variant and a method of producing 5'-inosinic acid using the same. The PTS transporter subunit EIIC variant is obtained by substituting one or more amino acids in the amino acid sequence constituting PTS transporter subunit EIIC to change the activity of the protein, and a recombinant microorganism comprising the PTS transporter subunit EIIC variant is capable of efficiently producing 5'-inosinic acid.

2 Claims, 1 Drawing Sheet

Specification includes a Sequence Listing.

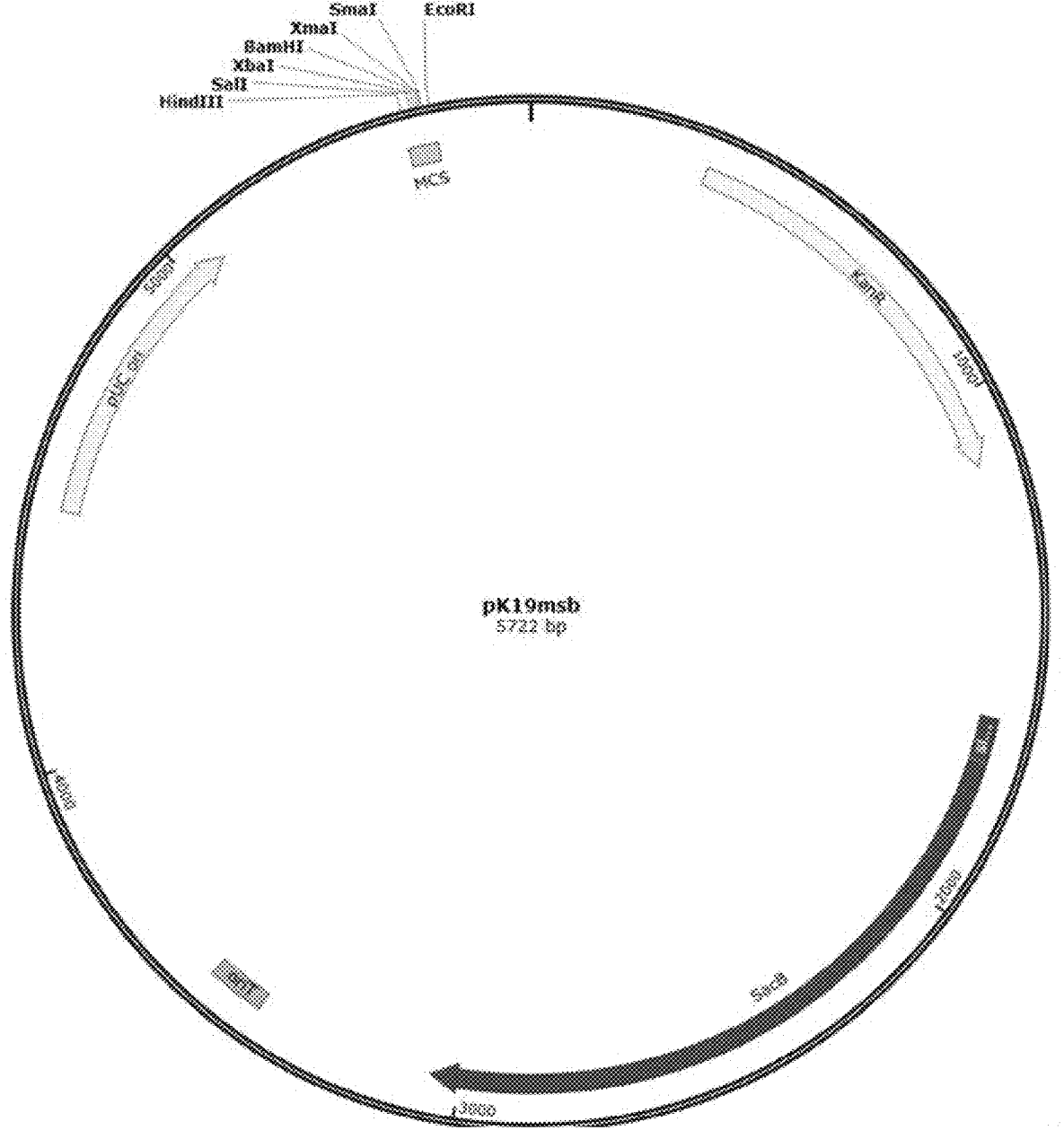

RECOMBINANT ORGANISM AND METHOD

SEQUENCE LISTING

A sequence listing in electronic (XML file) format is filed with this application and incorporated herein by reference. The name of the XML file is "Sequence Listing-1949A.xml"; the file was created on Dec. 30, 2024; the size of the file is 20,054 bytes.

TECHNICAL FIELD

The present invention relates to a novel PTS transporter subunit EIIC variant and a method of producing 5'-inosinic acid using the same.

BACKGROUND ART

5'-inosinic acid (or inosine monophosphate (IMP)) is an intermediate in the metabolic system of nucleic acid bio-synthesis, and not only plays an important physiological role in the bodies of plants and animals, but is also used in various applications, including food, medicine, and various medical applications. In particular, 5'-inosinic acid is a nucleic acid-based seasoning, which has drawn much attention as a savory seasoning, because it has significant synergistic effects on taste when used together with monosodium glutamate (MSG)

Methods for producing 5'-inosinic acid include a method of enzymatically degrading ribonucleic acid extracted from yeast cells, a method of chemically phosphorylating inosine produced by fermentation, etc.

Recently, a method of culturing a 5'-inosinic acid-microorganism and recovering 5'-inosinic acid producing accumulated in the medium has been mainly used.

For the production of 5'-inosinic acid using microorganisms, in order to improve the efficiency of production of 5'-inosinic acid, there has been development of a variety of recombinant strains or mutant strains having excellent 5'-inosinic acid productivity by applying genetic recombination technology to microorganisms such as *Escherichia coli* and *Corynebacterium*, which are widely used in the production of useful substances such as nucleic acids or L-amino acids, and methods of producing 5'-inosinic acid using the same. In particular, there have been attempts to increase the production of 5'-inosinic acid by targeting genes such as enzymes, transcription factors and transport proteins, which are involved in the biosynthetic pathway of 5'-inosinic acid, or by inducing mutations in promoters that regulate the expression of these genes. However, there are dozens to hundreds of types of proteins such as enzymes, transcription factors and transport proteins, which involved directly or are indirectly in the production of 5'-inosinic acid, and thus much research is still needed on the increase in 5'-inosinic acid productivity by changes in the activity of these proteins.

PRIOR ART DOCUMENTS

Patent Documents

Korean Patent No. 10-116602

DISCLOSURE

Technical Problem

An object of present invention is to provide a novel PTS transporter subunit EIIC variant.

Another object of the present invention is to provide a polynucleotide encoding the variant.

Still another object of the present invention is to provide a transformant comprising the variant Or polynucleotide.

Yet another object of the present invention is to provide a method of producing 5'-inosinic acid using the transformant.

Technical Solution

One aspect of the present invention provides a PTS transporter subunit EIIC variant consisting of the amino acid sequence of SEQ ID NO: 2 in which alanine at position 281 in the amino acid sequence of SEQ ID NO: 4 is substituted with valine.

As used in the present invention, the term "PTS transporter subunit EIIC" is a component of the phospho-enolpyruvate-dependent sugar phosphotransferase system (PTS), a major carbohydrate active transport system, and catalyzes the phosphorylation of incoming sugar substrates concomitantly with their translocation across the cell membrane, and it may be a polypeptide or protein consisting of the amino acid sequence of SEQ ID NO: 4 and having PTS transporter subunit EIIC activity.

Information on the nucleic acid and protein sequences of the PTS transporter subunit EIIC is available from known sequence databases (e.g., GenBank, UniProt), According to one embodiment of the present invention, the PTS transporter subunit EIIC may be encoded by the nucleotide sequence of SEQ ID NO: 3.

The amino acid sequence of the PTS transporter subunit EIIC according to the present invention or the nucleotide sequence encoding the same may include a nucleotide sequence or amino acid sequence having at least 70%, 75%, 80%, 85%, 90%, 95%, 96%, 97%, 98%, 99% or 100% homology or identity to the amino acid sequence of SEQ ID NO: 4 or the nucleotide sequence of SEQ ID NO: 3. As used herein, the term "identity" the "homology" or means percentage rate of identity between two sequences, which is determined by aligning the reference nucleotide sequence or amino acid sequence and any other nucleotide sequence or amino acid sequence to correspond to each other as much as possible and analyzing the aligned sequences.

According to one embodiment of the present invention, the PTS transporter subunit EIIC may be derived from wild-type *Corynebacterium stationis*.

As used in the present invention, the term "variant" refers to a protein that has an amino acid sequence different from the amino acid sequence before mutation by the conservative substitution and/or modification of one or more amino acids at the N-terminus, C-terminus of and/or within the amino acid sequence, which result(s) from mutation in the nucleotide sequence of the gene encoding the protein, but retains the functions or properties of the protein before mutation. As used herein, the term "conservative substitution" means substituting one amino acid with another amino acid having similar structural and/or chemical properties. The conservative substitution may have little or no impact on the activity of the protein or polypeptide. In addition, the term "modification" refers to substitution, insertion, deletion, or the like of one or more amino acids. The amino acid is selected from among alanine (Ala, A), isoleucine (Ile, I), valine (Val, V), leucine (Leu, L), methionine (Met, M), asparagine (Asn, N), cysteine (Cys, C), glutamine (Gln, Q), serine (Ser, S), threonine (Thr, T), phenylalanine (Phe, F), tryptophan (Trp, W), tyrosine (Tyr, Y), aspartic acid (Asp, D), glutamic acid (Glu, E), arginine (Arg, R), histidine (His, H), lysine (Lys, K), glycine (Gly, G), and proline (Pro, P).

In addition, some variants include those in which one or more portions, such as an N-terminal leader sequence or transmembrane domain, have been removed, or those in which a portion has been removed from the N- and/or C-terminus of a mature protein.

The variant may have increased (enhanced), unchanged, or decreased (weakened) ability compared to that of the protein before mutation, Here, the term "increased or enhanced" includes: a case in which the activity of the protein itself has increased compared to the activity of the protein before mutation; a case in which the overall activity of the protein in the cell is higher than that in the wild-type strain or the strain expressing the protein before mutation due to increased expression or translation of the gene encoding the protein; and a combination thereof. In addition, the term "decreased or weakened" includes: a case in which the activity of the protein itself has decreased compared to the activity of the protein before mutation; a case in which the overall activity of the protein in the cell is lower than that in the wild-type strain or the strain expressing the protein before mutation due to reduced expression or translation of the gene encoding the protein; and a combination thereof. In the present invention, the term "variant" may be used interchangeably with terms such as variant type, modification, variant polypeptide, mutated protein, mutation, and the like.

The PTS transporter subunit EIIC variant according to the present invention may comprise an amino acid sequence having at least 70%, 75%, 80%, 85%, 90%, 95%, 96%, 97%, 98%, 99% or 100% homology or identity to the amino acid sequence of SEQ ID NO: 2.

Another aspect of the present invention provides a polynucleotide encoding the PTS transporter subunit EIIC variant.

As used in the present invention, the term "polynucleotide" refers to a DNA or RNA strand having a certain length or more, which is a long-chain polymer of nucleotides formed by linking nucleotide monomers via covalent bonds, More specifically, the term "polynucleotide" refers to a polynucleotide fragment encoding the variant.

According to one embodiment of the present invention, the polynucleotide may comprise a nucleotide sequence encoding the amino acid sequence of SEQ ID NO: 2.

More specifically, the polynucleotide may comprise the nucleotide sequence of SEQ ID NO: 1 in which nucleotide "c" at position 842 in the nucleotide sequence of SEQ ID NO: 3 encoding PTS transporter subunit EIIC is substituted with nucleotide "t".

Still another aspect of the present invention provides a vector comprising a polynucleotide encoding the PTS transporter subunit EIIC variant.

Yet another aspect of the present invention provides a transformant comprising the PTS transporter subunit EIIC variant or the polynucleotide.

As used in the present invention, the term "vector" refers to any type of nucleic acid sequence transfer structure that is used as a means for transferring and expressing a gene of interest in a host cell. Unless otherwise specified, the "vector" one term may mean allowing the nucleic acid sequence contained therein to be expressed after insertion into the host cell genome and/or one allowing the nucleic acid sequence to be expressed independently. This vector comprises essential regulatory elements operably linked so that an inserted gene can be expressed. As used herein, the term "operably linked" means that a gene of interest and regulatory sequences thereof are functionally linked together in a manner enabling gene expression, and the "regulatory elements" include a promoter for initiating transcription, any operator sequence for regulating transcription, a sequence encoding suitable mRNA ribosome-binding sites, and a sequence for regulating termination of transcription and translation.

The vector in the present invention is not particularly limited as long as it may replicate in a host cell, and any vector known in the art may be used. Examples of the vector include a natural or recombinant plasmid, cosmid, virus and bacteriophage. Examples of a phage vector or cosmid vector include, but are not limited to, pWE15, M13, λMBL3, λMBL4, λIXII, λSHII, λAPII, λt10, λt11, Charon4A, and Charon21A, and examples of a plasmid vector include, but are not limited to, pBR series, pUC series, pBluescriptII series, pGEM series, pTZ series, pCL series, and pET series.

The vector may typically be constructed as a vector for cloning or as a vector for expression. The vector for expression may be a conventional vector that is used in the art to express a foreign gene or protein in a plant, animal, or microorganism, and may be constructed through various methods known in the art.

As used in the present invention, the term "recombinant vector" may be transformed into a suitable host cell, and then may replicate regardless of the genome of the host cell or may be integrated into the genome itself. In this case, the "suitable host cell" may contain a replication origin, which is a particular nucleotide sequence which enables the vector to replicate in the suitable host cell and from which replication starts. For example, when the vector used is an expression vector and uses a prokaryotic cell as a host, the vector generally comprises a strong promoter capable of promoting transcription (e.g., pLλpromoter, CMV promoter, trp promoter, lac promoter, tac promoter, T7 promoter, etc.), a ribosome binding site for initiation of translation, and a transcription/translation termination sequence. When a eukaryotic cell is used as a host, the vector comprises a replication origin operating in the eukaryotic cell, and examples of the replication origin include, but are not limited to, an f1 replication origin, an SV40 replication origin, a pMB1 replication origin, an adeno replication origin, an AAV replication origin, and a BBV replication origin. In addition, the recombinant vector may comprise a promoter derived from the genome of a mammalian cell (e.g., metallothionein promoter) or a promoter derived from a mammalian virus (e.g., adenovirus late promoter, vaccinia virus 7.5K promoter, SV40 promoter, cytomegalovirus promoter, HSV-tk promoter, etc.), and generally has a polyadenylation sequence as a transcription termination sequence.

The recombinant vector may comprise a selection marker. The selection marker serves to select a transformant (host cell) transformed with the vector, and since only cells expressing the selection marker can survive in the medium treated with the selection marker, it is possible to select transformed cells. Representative examples of the selection marker include, but are not limited to, kanamycin, streptomycin, and chloramphenicol.

The transformant may be produced by inserting the recombinant vector into a host cell, and the transformant may be obtained by introducing the recombinant vector into an appropriate host cell. The host cell is a cell capable of stably and continuously cloning or expressing the expression vector, and any host cell known in the art may be used.

Where the vector is transformed into prokaryotic cells to generate recombinant microorganisms, examples of host cells that may be used include, but are not limited to, *E. coli* sp. strains such as *E. coli* DH5α, *E. coli* JM109, *E. coli* BL21, *E. coli* RR1, *E. coli* LE392, *E. coli* B, *E. coli* X 1776,

5

*E. coli* W3110, and *E. coli* XL1-Blue, *Bacillus* sp, strains such as subtilis *Bacillus* and *Bacillus thuringiensis, Corynebacterium* sp. strains such as *Corynebacterium glutamicum* and *Corynebacterium stationis*, and various Enterobacteriaceae strains such as *Salmonella typhimurium, Serratia marcescens*, and *Pseudomonas* species.

Where the vector is transformed into eukaryotic cells to generate recombinant microorganisms, examples of host cells that may be used include, but are not limited to, yeast (e.g., *Saccharomyces cerevisiae*), insect cells, plant cells and animal cells, such as Sp2/0, CHO K1, CHO DG44; PER.C6, W138, BHK, COS7, 293, HepG2, Huh7, 3T3, RIN, and MDCK cell lines.

As used in the present invention, the term "transformation" refers to a phenomenon in which external DNA is introduced into a host cell, thereby artificially causing genetic changes, and the term "transformant" refers to a host cell into which external DNA has been introduced and in which the expression of the gene of interest is stably maintained.

The transformation may be performed using a suitable vector introduction technique selected depending on the host cell, so that the gene of interest or a recombinant vector comprising the same may be expressed in the host cell. For example, introduction of the vector may be performed by electroporation, heat-shock, calcium phosphate (CaPO$_4$) precipitation, calcium chloride (CaCl$_2$) precipitation, microinjection, polyethylene glycol (PEG) method, DEAE-dextran method, cationic liposome method, lithium acetate-DMSO method, or any combination thereof, without being limited thereto. As long as the transformed gene may be expressed in the host cell, it may be inserted into the chromosome of the host cell, or may exist extrachromosomally, without being limited thereto.

The transformant may include a cell transfected, transformed, or infected with the recombinant vector of the present invention in vivo or in vitro, and may be used in the same sense as a recombinant host cell, a recombinant cell, or a recombinant microorganism.

Genes inserted into the recombinant vector of the present invention may be introduced into a host cell such as a *Corynebacterium* sp. strain by homologous recombination crossover.

According to one embodiment of the present invention, the transformant may be a *Corynebacterium* sp. microorganism. The *Corynebacterium* sp. microorganism may be, but is not limited to, *Corynebacterium glutamicum, Corynebacterium crudilactis, Corynebacterium deserti, Corynebacterium callunae, Corynebacterium suranareeae, Corynebacterium lubricantis, Corynebacterium doosanense, Corynebacterium efficiens, Corynebacterium uterequi, Corynebacterium stationis, Corynebacterium pacaense, Corynebacterium singulare, Corynebacterium humireducens, Corynebacterium marinum, Corynebacterium halotolerans, Corynebacterium spheniscorum, Corynebacterium freiburgense, Corynebacterium striatum, Corynebacterium canis, Corynebacterium ammoniagenes, Corynebacterium renale, Corynebacterium pollutisoli, Corynebacterium imitans, Corynebacterium caspium, Corynebacterium testudinoris, Corynebacaterium pseudopelargi*, or *Corynebacterium flavescens*.

The transformant in the present invention may be a strain either comprising the above-described PTS transporter subunit EIIC variant or a polynucleotide encoding the same or comprising the vector comprising the same, a strain expressing the PTS transporter subunit EIIC variant or the polynucleotide, or a strain having activity for the PTS transporter subunit EIIC variant, without being limited thereto.

The transformant of the present invention may comprise other protein variants or genetic mutations, in addition to the PTS transporter subunit EIIC variant.

According to one embodiment of the present invention, the transformant may have the ability to produce 5'-inosinic acid.

The 5'-inosinic acid is a nucleic acid-based compound that gives flavor to food, especially umami (savory) taste, and is used with the same meaning as inosine monophosphate (IMP).

The transformant may naturally have the ability to produce 5'-inosinic acid or may be one artificially endowed with the ability to produce 5'-inosinic acid.

According to one embodiment of the present invention, the transformant may have an increased ability to produce 5'-inosinic acid, due to a change in PTS transporter subunit EIIC activity.

As used in the present invention, the term "increased ability to produce" means that 5'-inosinic acid productivity has increased compared to that of the parent strain. As used herein, the term "parent strain" refers to a wild-type strain or mutant strain to be mutated, and includes a strain that is to be mutated directly or to be transformed with a recombinant vector or the like. In the present invention, the parent strain may be a wild-type *Corynebacterium* sp. strain or a *Corynebacterium* sp. strain mutated from the wild-type strain.

The transformant according to the present invention exhibits an increased ability to produce 5'-inosinic acid compared to the parent strain, due to the change in PTS transporter subunit EIIC activity caused by introduction of the PTS transporter subunit EIIC variant thereinto. More specifically, the amount of 5'-inosinic acid produced by the transformant may be at least 18, 5%, 108, 15%, 20%, 25%, 30%, 35%, 40%, 45%, 50%, 55%, 60%, 65%, 70%, 75%, 80%, 85%, 90%, 95%, or 100% higher than that produced by the parent strain, or may be 1.1-fold, 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, or 10-fold higher than that produced by the parent strain, without being limited thereto. For example, the amount of 5'-inosinic acid produced by the transformant comprising the PTS transporter subunit EIIC variant may be at least 5%, specifically 5 to 50% (preferably 10 to 40%) higher than that produced by the parent strain.

Still yet another aspect of the present invention provides a method for producing 5'-inosinic acid, comprising steps of: culturing the transformant in a medium; and recovering 5'-inosinic acid from the transformant or the medium in which the transformant has been cultured.

The culturing may be performed using a suitable medium and culture conditions known in the art, and any person skilled in the art may easily adjust and use the medium and the culture conditions. Specifically, the medium may be a liquid medium, without being limited thereto. Examples of the culturing method include, but are not limited to, batch culture, continuous culture, fed-batch culture, or a combination thereof.

According to one embodiment of the present invention, the medium should meet the requirements of a specific strain in a proper manner, and may be appropriately modified by a person skilled in the art. For culture media for *Escherichia* sp. strains, reference may be made to, but not limited to, a known document (Manual of Methods for General Bacteriology, American Society for Bacteriology, Washington D.C., USA, 1981).

According to one embodiment of the present invention, the medium may contain various carbon sources, nitrogen sources, and trace element components. Examples of carbon sources that may be used include: sugars and carbohydrates such as glucose, sucrose, lactose, fructose, maltose, starch, and cellulose; oils and fats such as soybean oil, sunflower oil, castor oil, and coconut oil; fatty acids such as palmitic acid, stearic acid, and linoleic acid; alcohols such as glycerol and ethanol; and organic acids such acetic acid. These substances may be used individually or as a mixture, without being limited thereto. Examples of nitrogen sources that may be used include peptone, yeast extract, meat extract, malt extract, corn steep liquor, soybean meal, urea, or inorganic compounds such as ammonium sulfate, ammonium chloride, ammonium phosphate, ammonium carbonate, and ammonium nitrate. The nitrogen sources may also be used individually or as a mixture, without being limited thereto. Examples of phosphorus sources that may be used include, but are not limited to, potassium dihydrogen phosphate or dipotassium hydrogen phosphate or the corresponding sodium-containing salts. In addition, the culture medium may contain, but is not limited to, metal salts such as magnesium sulfate or iron sulfate, which are required for growth. In addition, the culture medium may contain essential growth substances such as amino acids and vitamins. Moreover, suitable precursors may be used in the culture medium. The medium or individual components may be added to the culture medium batchwise or in a continuous manner by a suitable method during culturing, without being limited thereto.

According to one embodiment of the present invention, the pH of the culture medium may be adjusted by adding compounds such as ammonium hydroxide, potassium hydroxide, ammonia, phosphoric acid and sulfuric acid to the microorganism culture medium in an appropriate manner during the culturing. In addition, during the culturing, foaming may be suppressed using an anti-foaming agent such as a fatty acid polyglycol ester. Additionally, to keep the culture medium in an aerobic condition, oxygen or an oxygen-containing gas (for example, air) may be injected into the culture medium. The temperature of the culture medium may be generally 20° C. to 45° C., for example, 25° C. to 40° C. The culturing may be continued until a desired amount of a useful substance is produced. For example, the culturing time may be 10 hours to 160 hours.

According to one embodiment of the present invention, in the step of recovering 5'-inosinic acid from the cultured transformant the medium in which the transformant has been cultured, the produced 5'-inosinic acid may be collected or recovered from the medium using a suitable method known in the art depending on the culture method. Examples of a method that may be used to recover the produced 5'-inosinic acid include, but are not limited to, centrifugation, filtration, extraction, spraying, drying, evaporation, precipitation, crystallization, electrophoresis, fractional dissolution (e.g., ammonium sulfate precipitation), chromatography (e.g., ion exchange, affinity, hydrophobicity and size exclusion), and the like.

According to one embodiment of the present invention, the step of recovering 5'-inosinic acid may be performed by centrifuging the culture medium at a low speed to remove biomass and separating the obtained supernatant through ion-exchange chromatography.

According to one embodiment of the present invention, the step of recovering 5'-inosinic acid may include a process of purifying the 5'-inosinic acid.

Advantageous Effects

The PTS transporter subunit EIIC variant according to the present invention is obtained by substituting one or more amino acids in the amino acid sequence constituting PTS transporter subunit EIIC to change the activity of the protein, and a recombinant microorganism comprising the PTS transporter subunit EIIC variant is capable of efficiently producing 5'-inosinic acid.

BRIEF DESCRIPTION OF DRAWINGS

FIG. 1 shows the structure of a pk19msb plasmid according to one embodiment of the present invention.

MODE FOR INVENTION

Hereinafter, the present invention will be described in more detail. However, this description is merely presented by way of example to facilitate the understanding of the present invention, and the scope of the present invention is not limited by this exemplary description.

Example 1. Construction of Strain Expressing PTS Transporter Subunit EIIC Variant To evaluate the effect of a variant (SEQ ID NO: 2) having a substitution of valine (V) for alanine (A) at position 281 in the amino acid sequence of PTS transporter subunit EIIC (SEQ ID NO: 4) on the production of 5'-inosinic acid, the present inventors constructed a vector for expressing the PTS transporter subunit EIIC variant and a strain into which the vector has been introduced.

1-1. Construction of Vector for Expression of PTS Transporter Subunit EIIC Variant Using the genomic DNA of wild-type *Corynebacterium stationis* ATCC6872 as a template, PCR reactions were performed using a primer pair of primers 1 and 2 and a primer pair of primers 3 and 4, respectively. Thereafter, using the two PCR products as templates, overlapping PCR was performed using a primer pair of primers 1 and 4 to obtain a single fragment. The PCR fragment and a pK19msb plasmid (SEQ ID NO: 5) were treated with the restriction enzyme smaI (NEB) and ligated together using T4 ligase. The resulting plasmid was named pK_FP.

The PCR amplification was performed using Pfu PreMix (Bioneer) under the following conditions: denaturation at 95° C. for 5 min, and then 30 cycles, each consisting of 95° C. for 30 sec, 58° C. for 30 sec, and 72° C. for 1 min and 30 sec, followed by reaction at 72° C. for 5 min.

The primer sequences used for plasmid construction are shown in Table 1 below.

TABLE 1

| Primer name | SEQ ID NO. | Primer sequence (5'→3') |
|---|---|---|
| Primer 1 | 6 | CGGCAAAGCGCACCTGAAGA |
| Primer 2 | 7 | CCGCAGCAACGACTTCGTTCA |
| Primer 3 | 8 | TGAACGAAGTCGTTGCTGCGG |
| Primer 4 | 9 | TCCATGAGCCGATCCACATTGCG |

1-2. Construction of Mutant Strain into which PTS Transporter Subunit EIIC Variant has been Introduced An electrocompetent cell preparation method, modification of the method of van der Rest et al., was used as a method for transformation of *Corynebacterium stationis* KCCM13339P.

First, *Corynebacterium stationis* KCCM13339P was primarily cultured in 10 mL of 2YT medium (containing 16 g/l of tryptone, 10 g/l of yeast extract, and 5 g/l of sodium chloride) supplemented with 2% glucose, thus preparing a seed culture. Isonicotinic acid hydrazine at a concentration of 1 mg/ml and 2.5% glycine were added to 100 ml of 2YT medium free of glucose. Next, the seed culture was inoculated into the 2YT medium to reach an $OD_{610}$ value of 0.3, and then cultured at 30° C. and 180 rpm for 5 to 8 hours so that the $OD_{610}$ value reached 0.6 to 0.7. The culture was kept on ice for 30 minutes, and then centrifuged at 3,500 rpm at 4° C. for 10 minutes. Thereafter, the supernatant was discarded and the precipitated *Corynebacterium stationis* KCCM13339P was washed 4 times with a 10% glycerol solution and finally re-suspended in 0.5 ml of a 10% glycerol solution, thereby preparing Competent cells. Electroporation was performed using a Bio-Rad electroporator. The prepared competent cells and the constructed pK_FP vector were placed in an electroporation cuvette (0.2 mm), and then subjected to electroporation under conditions of 2.5 kV, 200Ω and 12.5 μF. Immediately after completion of the electroporation, 1 ml of regeneration (RG) medium (containing 18.5 g/l brain heart infusion and 0.5 M sorbitol) was added to the cells which were then heat-treated at 46° C. for 6 minutes. Next, the cells were cooled at room temperature, transferred into a 15-ml cap tube, incubated at 30° C. for 2 hours, and plated on a selection medium (containing 5 g/l tryptone, 5 g/l NaCl, 2.5 g/l yeast extract, 18.5 g/l brain heart infusion powder, 15 g/l agar, 91 g/l sorbitol, and 20 μg/l kanamycin). The cells were cultured at 30° C. for 72 hours, and the generated colonies were cultured in medium until the stationary phase to induce secondary recombination. Then, the cells were diluted to $10^{-5}$ to $10^{-7}$, and plated on an antibiotic-free plate medium (containing 10% sucrose), and a strain having no kanamycin resistance and grown on the medium containing 10% sucrose was selected and named IFP-1.

Experimental Example 1. Evaluation of 5'-Inosinic Acid Productivity of Strain Expressing PTS Transporter Subunit EIIC Variant 5'-Inosinic acid productivity was compared between the parent strain KCCM13339P and the mutant strain IFP-1 into which the PTS transporter subunit EIIC variant has been introduced.

Each strain (parent strain or mutant strain) was inoculated at 1% by volume into a 100-ml flask containing 10 mL of the medium for 5'-inosinic acid production shown in Table 2 below, and cultured with shaking at 200 rpm at 34° C. for 45 hours. After completion of the culturing, the Concentration of 5'-inosinic acid in medium was the measured using HPLC (Agilent), and the results are shown in Table 3 below.

TABLE 2

| Component | Content |
|---|---|
| Glucose | 70 g/L |
| $(NH_4)_2SO_4$ | 2 g/L |
| $MgSO_4$ | 1 g/L |
| Urea | 2 g/L |
| Yeast extract | 20 g/L |
| $KH_2PO_4$ | 2 g/L |
| $FeSO_4$ | 10 mg/L |
| $MnSO_4$ | 10 mg/L |
| Thiamine_HCl | 5 mg/L |
| biotin | 20 ug/L |
| Cystein | 20 mg/L |
| Bata-alanine | 20 mg/L |
| Adenine | 30 mg/L |

TABLE 3

| Strain | 5'-inosinic acid production (g/L) |
|---|---|
| KCCM13339P | 19.7 |
| IFP-1 | 23.2 |

As shown in Table 3 above, it was confirmed that the amount of 5'-inosinic acid produced by the mutant strain into which the PTS transporter subunit EIIC variant has been introduced was increased by about 18% compared to that produced by the parent due to substitution of alanine at position 281 with valine. These results suggest that introduction of a point mutation into PTS transporter subunit EIIC provides a significant effect on 5'-inosinic acid productivity.

So far, the present invention has been described with reference to the preferred embodiments. Those of ordinary skill in the art to which the present invention pertains will appreciate that the present invention may be embodied in modified forms without departing from the essential characteristics of the present invention. Therefore, the disclosed embodiments should be considered from an illustrative point of view, not from a restrictive point of view. The scope of the present invention is defined by the claims rather than the foregoing description, and all differences within the scope equivalent thereto should be construed as being included in the present invention

[Accession Number]

Depository Authority: Korean Culture Center of Microorganisms (KCCM)

Accession Number: KCCM13339P

Deposit Date: Mar. 29, 2023

The invention claimed is:

1. A recombinant microorganism for producing 5'-inosinic acid, wherein the recombinant microorganism is obtained by introducing into a *Corynebacterium* stationis deposited with accession number KCCM13339P a PTS transporter subunit EIIC variant consisting of the amino acid sequence of SEQ ID NO: 2.

2. A method for producing 5'-inosinic acid, comprising the steps of:
  culturing the recombinant microorganism of claim 1 in a medium; and
  recovering 5'-inosinic acid from the recombinant microorganism or the medium in which the recombinant microorganism has been cultured.

* * * * *

SEQUENCE LISTING

```
Sequence total quantity: 9
SEQ ID NO: 1          moltype = DNA  length = 2097
FEATURE               Location/Qualifiers
source                1..2097
                      mol_type = other DNA
                      organism = synthetic construct
SEQUENCE: 1
```

```
atggcatccg atattattag aactgactta gtcgctttag acgcagactt aggcacctca   60
gttgaatcag taattaccca actagccacg ttagttcacg acgctggtcg cgccagcaac  120
gtggaagaat tagcgcgtcc cgcaattgag cgtgaggccc aagctggcac cggagtgcct  180
ggcaaggtag caatcccgca ctgccgttcc gcagcagtga gcgagccaac cttggctttt  240
gcgcgacttt ctcaagcggt agatttcgca ggtcctgatg gcgatgccga gttggtattt  300
ctgatcgctg ccccggaagg cggcggcaaa gcgcacctga agattctttc caagcttgcg  360
cgtgcactgg tgcgccagga tttcctcgac gcgcttcgta ctgcaagctc agaagaagaa  420
atcgtcgctt tagttagcga tgtcgtcagc gccgaaaaga aagcaccgac cagtgcaagc  480
tcaggtccaa cagagggggc gtcgacgaac gaggcatcga caagcgaagc atcgacaagc  540
actgcgaaag ctttgaacat tgttgctgtc accgcctgcc ccacaggtat tgctcacacc  600
tacatggctg ccgacgccct gagccaaacc gcagaaaagc gcgatgacat caaactcacg  660
gtagaaaccc aaggctcgtc caataacacc ccggttgcac aatcggtcat cgacgccgct  720
gatgccgtaa tcttcgctac cgatgtggga gtacgcgacc gcgaacgctt cgctggaaaa  780
cccgtcatcg aatccggtgt aaaacgcgct atcaacgaac ctgatgtcat gctgaacgaa  840
gtcgttgctg cggcgcaaaa ccctaactca cacaaggtta gcggtagcgc agcaatctct  900
tctggcacgg aggataccgc tagccagctc agctggggca gcgcatcca gcaggccgta   960
atgaccggtg tgtcctacat ggtgcccttc gtagccgctg cgcgtttgct actagcactg  1020
ggcttttat tcggaggcgc cgatatggcc aatggctgg aggccatctc tacccagtat  1080
tcactgacca acctgccggg gcacgaggtc gacgtcgacg gtgagctcct cagctttgaa  1140
cgctctggac tcctgctata tatcggcgcg gtgctctttg ccaccggcca agcctccatg  1200
ggctttatcg tctcagccct atctggctat attgcttacg ctttggctgg cgcgcctggt  1260
atcgcgccgg gctttgctgg cggcgcaatc gctgtcaccg tcggcgccgg cttcatcggt  1320
ggtctggtca caggtctact cgcgggtctt atcgcaatgt ggatcggctc atggaaggtg  1380
ccgcgctgga tgaattcttt aatgccagtg atgctcattc cgctgttgac cacttttggtg  1440
gttggtctcg caatgtactt cgtgctgggc gcaccgctgg aagcgttgat gactggcctg  1500
caaaacatgc ttggtggcat gtctggttct tctgcccgtag tgctgggcat cgtgctgggc  1560
ctaatgatgt gttctgacct gggtggccca attaataagg ctgcctacct cttcggtacc  1620
gcagggcttt ccaccggtga tcaagcatcc ctggaaatca tggcagcgat catggcctcc  1680
ggtatggttc caccaattgc tttgtcgatt gcaaccatcg tgcgcaagaa cctctttacc  1740
cctgcggagc aagaaaacgg caagtcttcc tggctgatgg gtctggcctt cgtctccgag  1800
ggcgcgattc cattcgctgc tgccgaccca ttccgcgtca ttccagcgat gatggctggt  1860
ggcgccacta ccggtgcgct catcatggca ctcggtgtgg gctcacgtgc tccgcacggt  1920
ggtatcttcg tgctctttgc tatcgaacct atctggggct acatcgttgc catcctggtc  1980
ggtactttgg ttgcggctgt cgccgtcatc gctttgaagc aattttggcc aaataagacc  2040
atccaggaag cagcagcaaa agatgcacga gaaaaatcag ccctcgcagc tgcttaa     2097
```

```
SEQ ID NO: 2            moltype = AA   length = 698
FEATURE                 Location/Qualifiers
source                  1..698
                        mol_type = protein
                        organism = synthetic construct
SEQUENCE: 2
MASDIIRTDL VALDADLGTS VESVITQLAT LVHDAGRASN VEELARPAIE REAQAGTGVP   60
GKVAIPHCRS AAVSEPTLAF ARLSQAVDFA GPDGDAELVF LIAAPEGGGK AHLKILSKLA  120
RALVRQDFLD ALRTASSEEE IVALVSDVVS AEKKAPTSAS SGPTEGASTN EASTSEASTS  180
TAKALNIVAV TACPTGIAHT YMAADALSQT AEKRDDIKLT VETQGSSNNT PVAQSVIDAA  240
DAVIFATDVG VRDRERFAGK PVIESGVKRA INEPDVMLNE VVAAAQNPNS HKVSGSAAIS  300
SGTEDTASQL SWGKRIQQAV MTGVSYMVPF VAAGGLLLAL GFLFGGADMA NGWQAISTQY  360
SLTNLPGHEV DVDGELLSFE RSGLLLYIGA VLFATGQASM GFIVSALSGY IAYALAGRPG  420
IAPGFAGGAI AVTVGAGFIG GLVTGLLAGL IAMWIGSWKV PRWMNSLMPV MLIPLLTTLV  480
VGLAMYFVLG APLEALMTGL QNMLGGMSGS SAVVLGIVLG LMMCSDLGGP INKAAYLFGT  540
AGLSTGDQAS LEIMAAIMAS GMVPPIALSI ATIVRKNLFT PAEQENGKSS WLMGLAFVSE  600
GAIPFAAADP FRVIPAMMAG GATTGALIMA LGVGSRAPHG GIFVLFAIEP IWGYIVAILV  660
GTLVAAVAVI ALKQFWPNKT IQEAAAKDAR EKSALAAA                          698
```

```
SEQ ID NO: 3            moltype = DNA   length = 2097
FEATURE                 Location/Qualifiers
source                  1..2097
                        mol_type = genomic DNA
                        organism = Corynebacterium stationis
SEQUENCE: 3
atggcatccg atattattag aactgactta gtcgctttag acgcagactt aggcacctca   60
gttgaatcag taattaccca actagccacg ttagttcacg acgctggtcg cgccagcaac  120
gtggaagaat tagcgcgtcc cgcaattgag cgtgaggccc aagctggcac cggagtgcct  180
ggcaaggtag caatcccgca ctgccgttcc gcagcagtga gcgagccaac cttggctttt  240
gcgcgacttt ctcaagcggt agatttcgca ggtcctgatg gcgatgccga gttggtattt  300
ctgatcgctg ccccggaagg cggcggcaaa gcgcacctga agattctttc caagcttgcg  360
cgtgcactgg tgcgccagga tttcctcgac gcgcttcgta ctgcaagctc agaagaagaa  420
atcgtcgctt tagttagcga tgtcgtcagc gccgaaaaga aagcaccgac cagtgcaagc  480
tcaggtccaa cagagggggc gtcgacgaac gaggcatcga caagcgaagc atcgacaagc  540
actgcgaaag ctttgaacat tgttgctgtc accgcctgcc ccacaggtat tgctcacacc  600
tacatggctg ccgacgccct gagccaaacc gcagaaaagc gcgatgacat caaactcacg  660
gtagaaaccc aaggctcgtc caataacacc ccggttgcac aatcggtcat cgacgccgct  720
gatgccgtaa tcttcgctac cgatgtggga gtacgcgacc gcgaacgctt cgctggaaaa  780
cccgtcatcg aatccggtgt aaaacgcgct atcaacgaac ctgatgtcat gctgaacgaa  840
gccgttgctg cggcgcaaaa ccctaactca cacaaggtta gcggtagcgc agcaatctct  900
tctggcacgg aggataccgc tagccagctc agctggggca gcgcatcca gcaggccgta   960
atgaccggtg tgtcctacat ggtgcccttc gtagccgctg cgcgtttgct actagcactg  1020
ggcttttat tcggaggcgc cgatatggcc aatggctgg aggccatctc tacccagtat  1080
```

-continued

```
tcactgacca acctgccggg gcacgaggtc gacgtcgacg gtgagctcct cagctttgaa  1140
cgctctggac tcctgctata tatcggcgcg gtgctctttg ccaccggcca agcctccatg  1200
ggctttatcg tctcagccct atctggctat attgcttacg ctttggctgg gcgccctggt  1260
atcgcgccgg gctttgctgg cggcgcaatc gctgtcaccg tcggcgccgg cttcatcggt  1320
ggtctggtca caggtctact cgcgggtgct atcgcaatgt ggatcggctc atggaaggtg  1380
ccgcgctgga tgaattcttt aatgccagtg atgctcattc cgctgttgac cactttggtg  1440
gttggtctcg caatgtactt cgtgctgggc gcaccgctgg aagcgttgat gactggcctg  1500
caaaacatgc ttggtggcat gtctggttct tctgccgtgg tgctgggcat cgtgctgggc  1560
ctaatgatgt gttctgacct gggtggccca attaataagg ctgcctacct cttcggtacc  1620
gcagggcttt ccaccggtga tcaagcatcc ctggaaatca tggcagcgat catggcctcc  1680
ggtatggttc caccaattgc tttgtcgatt gcaaccatcg tgcgcaagaa cctctttacc  1740
cctgcggagc aagaaaacgg caagtcttcc tggctgatgg gtctggcctt cgtctccgag  1800
ggcgcgattc cattcgctgc tgccgaccca ttccgcgtca ttccagcgat gatggctggt  1860
ggcgccacta ccggtgcgct catcatggca ctcggtggcg gctcacgtgc tccgcacggt  1920
ggtatcttcg tgctctttgc tatcgaacct atctgggggct acatcgttgc catcctggtc  1980
ggtactttg ttgcggctgt cgccgtcatc gctttgaagc aatttttggcc aaataagacc  2040
atccaggaag cagcagcaaa agatgcacga gaaaaatcag ccctcgcagc tgcttaa    2097
```

SEQ ID NO: 4          moltype = AA  length = 698
FEATURE              Location/Qualifiers
source               1..698
                    mol_type = protein
                    organism = Corynebacterium stationis
SEQUENCE: 4

```
MASDIIRTDL VALDADLGTS VESVITQLAT LVHDAGRASN VEELARPAIE REAQAGTGVP  60
GKVAIPHCRS AAVSEPTLAF ARLSQAVDFA GPDGDAELVF LIAAPEGGGK AHLKILSKLA  120
RALVRQDFLD ALRTASSEEE IVALVSDVVS AEKKAPTSAS SGPTEGASTN EASTSEASTS  180
TAKALNIVAV TACPTGIAHT YMAADALSQT AEKRDDIKLT VETQGSSNNT PVAQSVIDAA  240
DAVIFATDVG VRDRERFAGK PVIESGVKRA INEPDVMLNE AVAAAQNPNS HKVSGSAAIS  300
SGTEDTASQL SWGKRIQQAV MTGVSYMVPF VAAGGLLLAL GFLFGGADMA NGWQAISTQY  360
SLTNLPGHEV DVDGELLSFE RSGLLLYIGA VLFATGQASM GFIVSALSGY IAYALAGRPG  420
IAPGFAGGAI AVTVGAGFIG GLVTGLLAGL IAMWIGSWKV PRWMNSLMPV MLIPLLTTLV  480
VGLAMYFVLG APLEALMTGL QNMLGGMSGS SAVVLGIVLG LMMCSDLGGP INKAAYLFGT  540
AGLSTGDQAS LEIMAAIMAS GMVPPIALSI ATIVRKNLFT PAEQENGKSS WLMGLAFVSE  600
GAIPFAAADP FRVIPAMMAG GATTGALIMA LGVGSRAPHG GIFVLFAIEP IWGYIVAILV  660
GTLVAAVAVI ALKQFWPNKT IQEAAAKDAR EKSALAAA              698
```

SEQ ID NO: 5          moltype = DNA  length = 5719
FEATURE              Location/Qualifiers
source               1..5719
                    mol_type = other DNA
                    organism = synthetic construct
SEQUENCE: 5

```
tgccgcaagc actcagggcg caagggctgc taaaggaagc ggaacacgta gaaagccagt  60
ccgcagaaac ggtgctgacc ccggatgaat gtcagctact gggctatctg gacaagggaa  120
aacgcaagcg caaagagaaa gcaggtagct tgcagtgggc ttacatggcg atagctagac  180
tgggcggttt tatggacagc aagcgaaccg gaattgccag ctggggcgcc ctctggtaag  240
gttgggaagc cctgcaaagt aaactggatg gctttcttgc cgccaaggat ctgatggcgc  300
aggggatcaa gatctgatca agagacagga tgaggatcgt ttcgcatgat tgaacaagat  360
ggattgcacg caggttctcc ggccgcttgg gtggagaggc tattcggcta tgactgggca  420
caacagacaa tcggctgctc tgatgccgcc gtgttccggc tgtcagcgca ggggcgcccg  480
gttctttttg tcaagaccga cctgtccggt gccctgaatg aactccaaga cgaggcagcg  540
cggctatcgt ggctggccac gacgggcgtt ccttgcgcag ctgtgctcga cgttgtcact  600
gaagcgggaa gggactggct gctattgggc gaagtgccgg ggcaggatct cctgtcatct  660
caccttgctc ctgccgagaa agtatccatc atggctgatg caatggcgcg gctgcatacg  720
cttgatccgg ctacctgccc attcgaccac caagcgaaac atcgcatcgg cgagcacgt  780
actcggatgg aagccggtct tgtcgatcag gatgatctgg acgaagagca tcaggggctc  840
gcgccagccg aactgttcgc caggctcaag gcgcggatgc ccgacggcga ggatctcgtc  900
gtgacccatg gcgatgcctg cttgccgaat atcatggtgg aaaatggccg cttttctggc  960
ttcatcgact gtggccggct gggtgtggcg gaccgctatc aggacatagc gttggctacc  1020
cgtgatattg ctgaagagct tggcggcgaa tgggctgacc gcttcctcgt gctttacggt  1080
atcgccgctc ccgattcgca gcgcatcgcc ttctatcgcc ttcttgacga gttcttctga  1140
gcgggactct ggggttcgct agaggatcga tccttttaa cccatcacat atacctgccg  1200
ttcactatta tttagtgaaa tgagatatta tgatattttc tgaattgtga ttaaaaaggc  1260
aactttatgc ccatgcaaca gaaactataa aaaatacaga gaatgaaaag aaacagatag  1320
attttttagt tctttaggcc cgtagtctgc aaatccttt atgattttct atcaaacaaa  1380
agaggaaaat agaccagttg caatccaaac gagagtctaa tagaatgagg tcgaaaagta  1440
aatcgcgcgg gtttgttact gataaagcag gcaagaccta aaatgtgtaa agggcaaagt  1500
gtatactttg gcgtcacccc ttacatattt taggtctttt tttattgtgc gtaactaact  1560
tgccatcttc aaacaggagg gctggaagaa gcagaccgct aacacagtac ataaaaaagg  1620
agacatgaac gatgaacatc aaaaagtttg caaaacaagc aacagtatta acctttacta  1680
ccgcactgct ggcaggaggc gcaactcaag cgtttgcgaa agaaacgaac caaaagccat  1740
ataaggaaac atacggcatt cccatatta cacgccatga tatgctgcaa atccctgaac  1800
agcaaaaaaa tgaaaaatat caagtttctg aatttgattc gtccacaatt aaaaatatct  1860
cttctgcaaa aggcctggac gtttgggaca gctggccatt acaaaacgct gacggcactg  1920
tcgcaaacta tcacggctac cacatcgtct ttgcattagc cggagatcct aaaaatgcgg  1980
atgcacatc gatttacatg ttctatcaaa aagtcggcga aacttctatt gacagctgga  2040
aaaacgctgg ccgcgtcttt aaagacagcg acaaattcga tgcaaatgat tctatcctaa  2100
aagaccaaac acaagaatgg tcaggttcag ccacatttac atctgacgga aaaatccgtt  2160
```

-continued

```
tattctacac tgatttctcc ggtaaacatt acggcaaaca aacactgaca actgcacaag    2220
ttaacgtatc agcatcagac agctctttga acatcaacgg tgtagaggat tataaatcaa    2280
tctttgacgg tgacggaaaa acgtatcaaa atgtacagca gttcatcgat gaaggcaact    2340
acagctcagg cgacaaccat acgctgagag atcctcacta cgtagaagat aaaggccaca    2400
aatacttagt atttgaagca aacactggaa ctgaagatgg ctaccaaggc gaagaatctt    2460
tatttaacaa agcatactat ggcaaaagca catcattctt ccgtcaagaa agtcaaaaac    2520
ttctgcaaag cgataaaaaa cgcacggctg agttagcaaa cggcgctctc ggtatgattg    2580
agctaaacga tgattacaca ctgaaaaaag tgatgaaacc gctgattgca tctaacacag    2640
taacagatga aattgaacgc gcgaacgtct ttaaaatgaa cggcaaatgg tacctgttca    2700
ctgactcccg cggatcaaaa atgacgattg acggcattac gtctaacgat atttacatgc    2760
ttggttatgt ttctaattct ttaactggcc catacaagcc gctgaacaaa actggccttg    2820
tgttaaaaat ggatcttgat cctaacgatg taacctttac ttactcacac ttcgctgtac    2880
ctcaagcgaa aggaaacaat gtcgtgatta caagctatat gacaaacaga ggattctacg    2940
cagacaaaca atcaacgttt gcgccgagct tcctgctgaa catcaaaggc aagaaaacat    3000
ctgttgtcaa agacagcatc cttgaacaag gacaattaac agttaacaaa taaaaacgca    3060
aaagaaaatg ccgatgggta ccgagcgaaa tgaccgacca agcgacgccc aacctgccat    3120
cacgagattt cgattccacc gccgccttct atgaaaggtt gggcttcgga atcgtttccc    3180
gggacgccct cgcggacgtg ctcatagtcc acgacgcccg tgattttgta gccctggccg    3240
acggccagca ggtaggccga caggctcatg ccggccgccg ccgccttttc ctcaatcgct    3300
cttcgttcgt ctggaaggca gtacaccttg ataggtgggc tgcccttcct ggttggcttg    3360
gtttcatcag ccatccgctt gccctcatct gttacgccgg cggtagccgg ccagcctcgc    3420
agagcaggat tcccgttgag caccgccagg tgcgaataag gagcagtgaa gaaggaacac    3480
ccgctcgcgg gtgggcctac ttcacctatc ctgcccggct gacgccgttg gatacaccaa    3540
ggaaagtcta cacgaaccct ttggcaaaat cctgtatatc gtgcgaaaaa ggatggatat    3600
accgaaaaaa tcgctataat gaccccgaag cagggttatg cagcggaaaa gcgctgcttc    3660
cctgctgttt tgtggaatat ctaccgactg gaaacgactg aatgcaggaa attactgaac    3720
tgaggggaca ggcgagagac gatgccaaag agctcctgaa aatctcgata actcaaaaaa    3780
tacgcccggt agtgatctta tttcattatg gtgaaagttg gaacctctta cgtgccgatc    3840
aacgtctcat tttcgccaaa agttggccca gggcttcccg gtatcaacag ggacaccagg    3900
atttatttat tctgcgaagt gatcttccgt cacaggtatt tattcggcgc aaagtgcgtc    3960
gggtgatgct gccaacttac tgatttagtg tatgatggtg ttttttgaggt gctccagtgg    4020
cttctgtttc tatcagctcc tgaaaatctc gataactcaa aaaatacgcc cggtagtgat    4080
cttatttcat tatggtgaaa gttggaacct cttacgtgcc gatcaacgtc tcattttcgc    4140
caaaagttgg cccagggctt cccggtatca acagggattat ttattctgcg    4200
aagtgatctt ccgtcacagg tatttattat gcgcaaagtg cgtcgggtga tgctgccaag    4260
ttactgattt agtgtatgat ggtgtttttg aggtgctcca gtggcttctg tttctatcag    4320
ggctggatga tcctccagcg cggggatctc atgctggagt tcttcgccca ccccaaaagg    4380
atctaggtga agatcctttt tgataatctc atgaccaaaa tcccttaacg tgagttttcg    4440
ttccactgag cgtcagaccc cgtagaaaag atcaaaggat cttcttgaga tcctttttttg    4500
ctgcgcgtaa tctgctgctt gcaaacaaaa aaaccaccgc taccagcggt ggtttgtttg    4560
ccggatcaag agctaccaac tctttttccg aaggtaactg gcttcagcag agcgcagata    4620
ccaaatactg ttcttctagt gtagccgtag ttaggccacc acttcaagaa ctctgtagca    4680
ccgcctacat acctcgctct gctaatcctg ttaccagtgg ctgctgccag tggcgataag    4740
tcgtgtctta ccgggttgga ctcaagacga tagttaccgg ataaggcgca gcggtcgggc    4800
tgaacggggg gttcgtgcac acagcccagc ttggagcgaa cgacctacac cgaactgaga    4860
tacctacagc gtgagctatg agaaagcgcc acgcttcccg aagggagaaa ggcggacagg    4920
tatccggtaa gcggcagggt cggaacagga gagcgcacga gggagcttcc aggggggaaac    4980
gcctggtatc tttatagtcc tgtcgggttt cgccacctct gacttgagcg tcgatttttg    5040
tgatgctcgt caggggggcg gagcctatgg aaaaacgcca gcaacgcggc cttttttacgg    5100
ttcctggcct tttgctggcc ttttgctcac atgttctttc ctgcgttatc ccctgattct    5160
gtggataacc gtattaccgc ctttgagtga gctgataccg ctcgccgcag ccgaacgacc    5220
gagcgcagcg agtcagtgag cgaggaagcg gaagagcgcc caatacgcaa accgcctctc    5280
cccgcgcgtt ggccgattca ttaatgcagc tggcacgaca ggtttcccga ctggaaagcg    5340
ggcagtgagc gcaacgcaat taatgtgagt tagctcactc attaggcacc ccaggcttta    5400
cactttatgc ttccggctcg tatgttgtgt ggaattgtga gcggataaca atttcacaca    5460
ggaaacagct atgacatgat tacgccaagc ttgcatgcct gcaggtcgac tctagaggat    5520
ccccgggtac cgagctcgaa ttcactggcc gtcgttttac aacgtcgtga ctgggaaaac    5580
cctggcgtta cccaacttaa tcgccttgca gcacatcccc ctttcgccag ctggcgtaat    5640
agcgaagagg cccgcaccga tcgcccttcc caacagttgc gcagcctgaa tggcgaatgg    5700
cgataagcta gcttcacgc                                                 5719
```

```
SEQ ID NO: 6              moltype = DNA  length = 20
FEATURE                  Location/Qualifiers
source                   1..20
                         mol_type = other DNA
                         organism = synthetic construct
SEQUENCE: 6
cggcaaagcg cacctgaaga                                                20

SEQ ID NO: 7              moltype = DNA  length = 21
FEATURE                  Location/Qualifiers
source                   1..21
                         mol_type = other DNA
                         organism = synthetic construct
SEQUENCE: 7
ccgcagcaac gacttcgttc a                                              21

SEQ ID NO: 8              moltype = DNA  length = 21
FEATURE                  Location/Qualifiers
```

-continued

```
source                  1..21
                        mol_type = other DNA
                        organism = synthetic construct
SEQUENCE: 8
tgaacgaagt cgttgctgcg g                                           21

SEQ ID NO: 9            moltype = DNA  length = 23
FEATURE                 Location/Qualifiers
source                  1..23
                        mol_type = other DNA
                        organism = synthetic construct
SEQUENCE: 9
tccatgagcc gatccacatt gcg                                         23
```